United States Patent [19]

Horvitz et al.

[11] 4,324,909
[45] Apr. 13, 1982

[54] PROCESS FOR PREPARING GLYCOLS AND GLYCOL ESTERS

[75] Inventors: David Horvitz; Thomas S. Brima, both of Cincinnati, Ohio

[73] Assignee: National Distillers & Chemical Corp., New York, N.Y.

[21] Appl. No.: 169,535

[22] Filed: Jul. 17, 1980

[51] Int. Cl.$^3$ .................... C07C 67/05; C07C 29/03
[52] U.S. Cl. ................................ 560/246; 568/860
[58] Field of Search ................... 568/860; 560/246

[56] References Cited

U.S. PATENT DOCUMENTS

| | | | |
|---|---|---|---|
| 3,479,395 | 11/1969 | Huguet | 568/860 |
| 3,985,795 | 8/1976 | Kollar | 560/246 |
| 4,095,037 | 6/1978 | Stapp | 560/246 |
| 4,195,190 | 3/1980 | Bierschenk et al. | 568/860 |
| 4,202,995 | 5/1980 | Mee | 568/860 |
| 4,205,181 | 5/1980 | Murib | 560/246 |
| 4,219,666 | 8/1980 | Platz et al. | 560/246 |

FOREIGN PATENT DOCUMENTS

| | | | |
|---|---|---|---|
| 2912956 | 10/1979 | Fed. Rep. of Germany | 568/860 |
| 729952 | 8/1932 | France | 568/860 |
| 54-22306 | 2/1979 | Japan . | |
| 2017692 | 10/1979 | United Kingdom | 568/860 |

*Primary Examiner*—Joseph E. Evans
*Attorney, Agent, or Firm*—Kenneth D. Tremain

[57] ABSTRACT

In the process for catalytically reacting olefin and oxygen to provide glycol or a mixture of glycol and glycol ester, higher rates of reaction and/or higher selectivities for the desired product(s) are obtained employing as catalyst, a composition comprising a mixture of molecular iodine and hydrobromic acid; hydriodic acid and hydrobromic acid; or, at least one oxide of antimony, bismuth or tellurium in admixture with at least one member of the group consisting of hydriodic acid; molecular iodine; hydriodic acid and molecular iodine; molecular iodine and hydrobromic acid; and, hydriodic acid and hydrobromic acid in a water or water-carboxylic acid reaction medium.

6 Claims, No Drawings

PROCESS FOR PREPARING GLYCOLS AND GLYCOL ESTERS

BACKGROUND OF THE INVENTION

1. Field of the Invention

This invention relates to catalyzed processes for the reaction of olefin and oxygen in a water or water-carboxylic acid reaction medium to provide the corresponding glycol and glycol ester.

2. Description of the Prior Art

It is known in the art to react an olefin with water and oxygen in the liquid phase in the presence of molecular iodine as catalyst to provide glycol. Illustrated for ethylene, the reaction may be represented as follows:

$$C_2H_4 + H_2O + \tfrac{1}{2} O_2 \xrightarrow{I_2} C_2H_4(OH)_2$$

This process is described in U.S. Pat. No. 1,982,545 to Skärblom which, in addition to molecular iodine, discloses other iodine-containing catalysts which provide elemental iodine under the conditions of the reaction, i.e., hydrogen iodide, ethylene iodide, potassium triiodide, ferric iodide and glycol iodinehydrine. According to U.S. Pat. No. 3,928,474 to Witheford, the co-production of excessive quantities of high boiling components such as diethylene glycol and triethylene glycol which results from the Skärblom process can be prevented by carrying out the above reaction at elevated temperature and superatmospheric pressure and thereafter recovering the product ethylene glycol by distillation carried out at subatmospheric pressure.

U.S. Pat. No. 4,088,286 to Hirose et al. describes a process for obtaining glycols from olefins of 2 to 4 carbon atoms in which the olefin is reacted with oxygen and water in the liquid phase at 100°–200° C. employing a catalyst containing copper and/or iron cations and an anion which at least includes a bromine ion which can solubilize copper and/or iron. The catalyst can be a copper bromide or an iron bromide itself or some other copper or iron compound together with a suitable source of solubilizing bromine anion, e.g., molecular bromine, hydrogen bromide or an organobromide. With limited exception, patentees strongly warn against conducting the reaction in the presence of molecular bromine or free hydrobromic acid as these species are said to be useless, even detrimental, to the process.

In a related process for obtaining glycol and/or glycol ester, olefin is reacted with oxygen and carboxylic acid, optionally in the presence of added water, employing any one of a variety of catalysts. The reaction, commonly referred to as oxyacylation, is usually carried out in the liquid phase at elevated temperature and superatmospheric pressure. Thus for the reaction of ethylene, oxygen and acetic acid to produce ethylene glycol diacetate, the overall chemical reaction can be considered to proceed in accordance with the reaction:

$$H_2C{=}CH_2 + \tfrac{1}{2} O_2 + 2\,CH_3COOH \xrightarrow[\substack{\text{elev. temp.}\\ \text{and pressure}}]{\text{catalyst}} H_3CCOOH_2CCH_2OOCCH_3 + H_2O$$

In addition to diester, this reaction will also result in the production of some monoester. Depending in large measure upon the catalyst employed, reactions other than the aforesaid oxyacylation reaction can take place, and to the extent they reduce product yield, complicate recovery and separation techniques and increase raw material and production costs, they are undesirable. It is, of course, recognized that simultaneous reaction of two different carboxylic acids will result in a mixture of products containing symmetrical diesters and unsymmetrical (mixed) diester. The alkylene glycol mono- and diesters are readily hydrolyzed to the glycols and to the carboxylic acid(s) employed in their production employing known and conventional techniques, e.g., hydrolysis and saponification with alkali followed by acid treatment.

Numerous proposals for oxyacylation catalysts have been made. U.S. Pat. No. 2,519,754 employs as catalyst, a hydrohalide such as hydrobromic acid or an organic acid capable of generating the free acid such as an aliphatic bromide. Snyder's process described in U.S. Pat. No. 2,701,813 employs certain metals or metal compounds such as silver, compounds of metals of the first transition group of the periodic system, particularly their salts, and salts of such heavy metals which are capable of existing in more than one oxidation state such as the acetates, stearates and naphthenates of cobalt, manganese, copper and the like. The olefin oxidation process of U.S. Pat. No. 3,427,348 to Olson employs selenium dioxide in admixture with a mineral acid such as hydrochloric acid. U.S. Pat. Nos. 3,479,395 and 3,637,515 to Huguet each describes a process employing tellurium dioxide solubilized with a halide salt. Lutz, in U.S. Pat. No. 3,542,857, employs a cerium (III) or cerium (IV) salt which is soluble in the carboxylic acid component of the oxyacylation reaction medium. U.S. Pat. Nos. 3,668,239 and 3,789,065 to Kollar, and U.S. Pat. No. 3,907,874 to Harvey et al. each employ a source of metal cation such as that of tellurium and a source of bromine. U.S. Pat. Nos. 3,689,535 and 3,985,795 to Kollar and U.S. Pat. No. 3,872,164 to Schmidt each describe a process for preparing ethylene glycol esters by contacting ethylene, bromine or chlorine, or compound of bromine or chlorine, and oxygen in the presence of a carboxylic acid and a variable metal cation such as antimony cation. Similarly, the Valbert (U.S. Pat. No. 3,715,388) and Hoch (U.S. Pat. No. 3,715,389) catalysts include bromine or a bromine compound and a source of metal cation such as arsenic or antimony cation. U.S. Pat. No. 3,770,813 to Kollar describes the use of a catalyst containing iodine or iodide anion and a heavy metal cation of atomic number 21–30 and 48. U.S. Pat. No. 3,778,468 employs a catalyst containing selenium cation and chlorine, bromine or a compound thereof. Gaenzler et al. U.S. Pat. No. 3,916,011 describe an oxyacylation catalyst which is a complex formed between a compound of titanium and a compound of lithium, beryllium, magnesium, calcium, boron, aluminum, silicon or phosphorus, or a complex formed between compounds of at least two of the elements boron, aluminum, silicon and phosphorus. The oxyacylation catalyst of Gaenzler et al. U.S. Pat. No. 3,981,908 contains a compound of boron, aluminum, silicon, phosphorus or a combination thereof, and a compound of iron, copper or a combination thereof. The Schmerling (U.S. Pat. No. 4,009,203) catalyst is the reaction product of a tin halide and a carboxylic acid.

Each of the aforesaid catalysts is subject to one or more disadvantages, either in regard to the complexity of the apparatus required to carry out the process and- /or in regard to the degree of selectivity of the reaction of olefin, oxygen and carboxylic acid for alkylene glycol ester.

SUMMARY OF THE INVENTION

In accordance with the present invention, alkylene glycols and alkylene glycol esters are prepared by reacting an alpha-olefin and oxygen in water or water-carboxylic acid reaction medium in the presence of a catalyst composition which is soluble under the conditions of the reaction comprising a mixture of molecular iodine and hydrobromic acid; hydriodic acid and hydrobromic acid; or, at least one oxide of antimony, bismuth or tellurium in admixture with at least one member of the group consisting of hydriodic acid; molecular iodine; hydriodic acid and molecular iodine; molecular iodine and hydrobromic acid; and, hydriodic acid and hydrobromic acid. When carboxylic acid is present as a part of the liquid water-carboxylic acid medium, the aforesaid process provides glycol ester of mixtures of glycol and glycol ester.

Employing the catalyst composition in the water or water-carboxylic acid medium of this invention, higher rates of reaction and/or higher selectivities for the desired glycol/glycol ester can be obtained compared with other catalysts and other solvent systems such as those referred to above.

DESCRIPTION OF THE PREFERRED EMBODIMENTS

The olefins which are useful in the process of this invention include monoolefins such as ethylene, propylene, butene-1, pentene-1, octene-1, decene-1, and the like, and diolefins of which butadiene is the most notable example. Ethylene and propylene are especially preferred due to their industrial importance and ready availability. The olefin as well as the other components of the reaction medium herein can contain impurities of the type and in the amounts normally present in industrial grades of the materials.

While for reasons of economy and practicability, the oxygen requirements of the reaction herein will usually be satisfied by air, other sources of oxygen such as molecular oxygen and air enriched with oxygen can also be used with good results.

The carboxylic acid contemplated herein is advantageously selected from the aliphatic monocarboxylic acids including formic, acetic, propionic, butyric, isobutyric, valeric, isovaleric, caproic, enanthic, caprylic, pelargonic, capric, lauric, myristic, palmitic, stearic, hexacosanoic, tricosanoic, cyclopropanecarboxylic, cyclopentanecarboxylic, hexahydrobenzoic, benzoic, 1-napthoic, 2-napthoic, ortho-toluic, meta-toluic, para-toluic, ortho-chlorobenzoic, meta-chlorobenzoic, para-chlorobenzoic, ortho-nitrobenzoic, meta-nitrobenzoic, para-hydroxybenzoic, anthranilic, meta-aminobenzoic, para-aminobenzoic, phenylbutyric, and the like. Acetic acid is especially preferred for use herein.

The molar ratios of olefin, water, oxygen and carboxylic acid can vary over a wide range but in general, it is preferred to employ a large stoichiometric excess of water, oxygen and carboxylic acid to favor maximum conversion of olefin per pass. Thus, for example, it is advantageous to use amounts of water, oxygen and carboxylic which exceed the stoichiometric requirements of the reaction by a factor of from about 1.5 to about 100 times the amount needed, and preferably by a factor of from about 2 to about 10 times the amount needed.

To obtain maximum conversion of the olfein to glycol and glycol ester products, it is preferred to utilize a water-carboxylic acid medium containing about 15 to 25% water. The use of water alone provides for the production of glycol in fair yield, but the overall conversion of olefin is less than in the preferred water-carboxylic acid reaction medium.

The catalyst composition of the present invention comprises a mixture of molecular iodine and hydrobromic acid; hydriodic acid and hydrobromic acid; or, at least one oxide of antimony, bismuth or tellurium such as antimony pentoxide ($Sb_2O_5$), bismuth trioxide ($Bi_2O_3$), bismuth tetroxide ($Bi_2O_4$) or tellurium dioxide ($TeO_2$), in admixture with at least one member of the group consisting of hydriodic acid; molecular iodine; hydriodic acid and molecular iodine; molecular iodine and hydrobromic acid; and, hydriodic acid and hydrobromic acid. In the aforesaid catalyst compositions, the weight ratio of molecular iodine or hydriodic acid to hydrobromic acid and the weight ratio of the antimony oxide, bismuth oxide and/or tellurium oxide to the remaining components making up the mixtures can range from about 1:10 to about 10:1, with weight ratios of from about 1:3 to about 3:1 being preferred. The amount of catalyst composition employed can vary considerably with the effective minimum concentration thereof being dependent upon temperature, residence time and the particular catalyst composition selected. From about 0.01 weight parts to about 1 weight part, and preferably from about 0.05 weight parts to about 0.1 weight parts, catalyst per hundred weight parts of olefin can be used with good results.

In general, any apparatus of the type suitable for carrying out oxidation reactions in the liquid phase, e.g., stirred autoclave and tubular reactors, can be used in carrying out the oxyacylation reaction of this invention. The reactor can be brought to the reaction temperature before or after the introduction of the reaction feed mixture. However, in a large-scale operation, it is preferred to carry out the process in a continuous manner and in such a system, the recirculation of unreacted olefin and optional carboxylic acid is contemplated. Provided a liquid phase reaction medium is maintained, the particular elevated temperature and superatmospheric pressures selected herein is not particularly critical. The practical limitations of production equipment will dictate to a great extent the selection of temperatures and pressure at which the reaction is to be effected. Thus, using available production systems, the selected elevated temperature should be at least about 75° C. and can range up to about 250° C. and even higher. For most purposes, the preferred operating temperature ranges from about 100° C. to about 175° C. The superatmospheric pressure should be at least about 5 atmospheres and can range up to almost any pressure attainable with the production apparatus. Since extremely high pressure apparatus is quite expensive, pressures to about 700 atmospheres are suggested. Most desirably, the pressure should be in the range of from about 10 to about 70 atmospheres, particularly when employing the aforesaid preferred temperature range.

The following examples are further illustrative of the process of the invention.

EXAMPLES 1 to 7

Ethylene and air at 200 psig were charged at ambient temperature to a reactor containing acetic acid and/or water and dissolved catalyst in the amounts indicated in Table I below. The reaction medium was heated to 160° C. for 7 hours and the amounts of reaction products, ethylene glycol (EG), ethylene glycol monoacetate (EGM) and ethylene glycol diacetate (EGD), were determined.

TABLE I

| Example | Catalyst (mmole) | Acetic Acid (ml) | Water (ml) | EG | EGM | EGD |
|---|---|---|---|---|---|---|
| 1 | 4.7 HI/4.7 HBr/1.5 $Sb_2O_5$ | 20 | 5 | 1.8 | 16.0 | 12.7 |
| 2 | 4.7 $I_2$/4.7 HBr | 20 | 5 | 0.3 | 7.8 | 6.6 |
| 3 | 4.7 $I_2$/4.7 HBr/1.5 $Sb_2O_5$ | 20 | 5 | 1.9 | 11.5 | 6.8 |
| 4 | 4.7 HBr | 25 | 0 | — | 0.5 | 2.9 |
| 5 | 7.1 $I_2$/4.7 HI/1.5 $Sb_2O_5$ | 0 | 25 | 14.4 | — | — |
| 6 | 7.2 HBr/1.5 $Sb_2O_5$ | 25 | 0 | — | 0.4 | 2.0 |
| 7 | 7.8 KBr/1.5 $Sb_2O_5$ | 25 | 0 | — | 0.7 | 9.8 |

In examples 1 to 3 and 5 which are illustrative of the process of this invention, excellent product yields were obtained. However, as shown in Examples 4, 6 and 7 demonstrating catalyst systems in the absence of water in the reaction media, the product yields were considerably less.

EXAMPLES 8 to 13

Premixed ethylene and air containing 5 weight percent oxygen was bubbled through an aqueous solution of acetic acid contained in a packed tubular reactor at 160° C. and 500 psig total pressure. The reaction media and the nonvolatile products were recycled to the reactor for the three hour reaction period of each example. The composition of the catalysts and the amounts of acetic acid, water and reaction products are given in Table II below.

TABLE II

| Example | Catalyst (mmole) | Acetic Acid (ml) | Water (ml) | EG | EGM | EGD |
|---|---|---|---|---|---|---|
| 8 | 7.1 HI | 20 | 5 | 3.4 | 10.2 | 9.0 |
| 9 | 18.8 HI/3.0 $Sb_2O_5$ | 40 | 10 | 1.4 | 17.4 | 20.1 |
| 10 | 18.8 HI/3.0 $Sb_2O_5$ | 40 | 10 | 2.2 | 28.5 | 17.9 |
| 11 | 18.8 HI/3.0 $Sb_2O_5$ | 40 | 10 | 1.8 | 24.6 | 15.4 |
| 12 | 25.9 HI/3.0 $Sb_2O_5$ | 40 | 10 | 1.1 | 20.4 | 13.6 |
| 13 | 18.6 HI/3.0 $Sb_2O_5$ | 40 | 10 | 4.0 | 23.6 | 13.7 |

These data show that in each example where antimony oxide was obtained with hydriodic acid as the catalyst agent in accordance with this invention, combined reaction product yields were almost twice as high as hydriodic acid catalyst used alone.

What is claimed is:

1. In the process for catalytically reacting olefin and oxygen in the liquid phase to provide saturated glycol or a mixture of saturated glycol and saturated glycol ester, the improvement which comprises employing as catalyst, a composition consisting essentially of at least one oxide of antimony or bismuth in admixture with at least one member of the group consisting of hydriodic acid; molecular iodine; hydriodic acid and molecular iodine; molecular iodine and hydrobromic acid; and, hydriodic acid and hydrobromic acid in a water or water-carboxylic acid reaction medium.

2. The process of claim 1 wherein the olefin is ethylene or propylene.

3. The process of claim 1 wherein the oxygen is supplied as air.

4. The process of claim 1 wherein the carboxylic acid is acetic acid.

5. The process of claim 1 wherein the weight ratio of the oxide of antimony or bismuth to the remaining component or components making up the catalyst composition is from about 1:10 to about 10:1.

6. The process of claim 5 wherein the weight ratio of the oxide of antimony or bismuth to the remaining component or components making up the catalyst composition is from about 1:3 to about 3:1.

* * * * *